Figure 1:
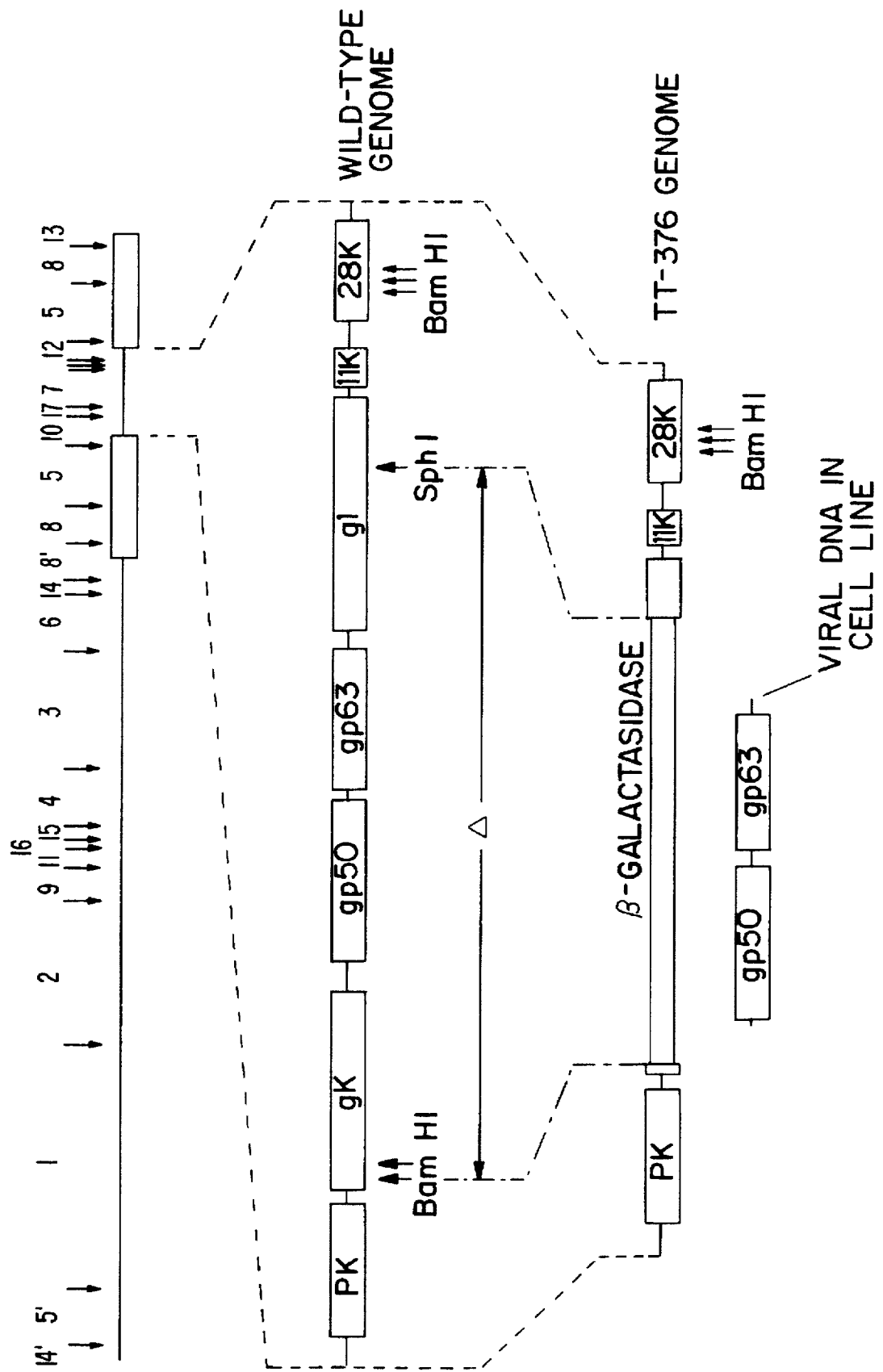
Figure 2:
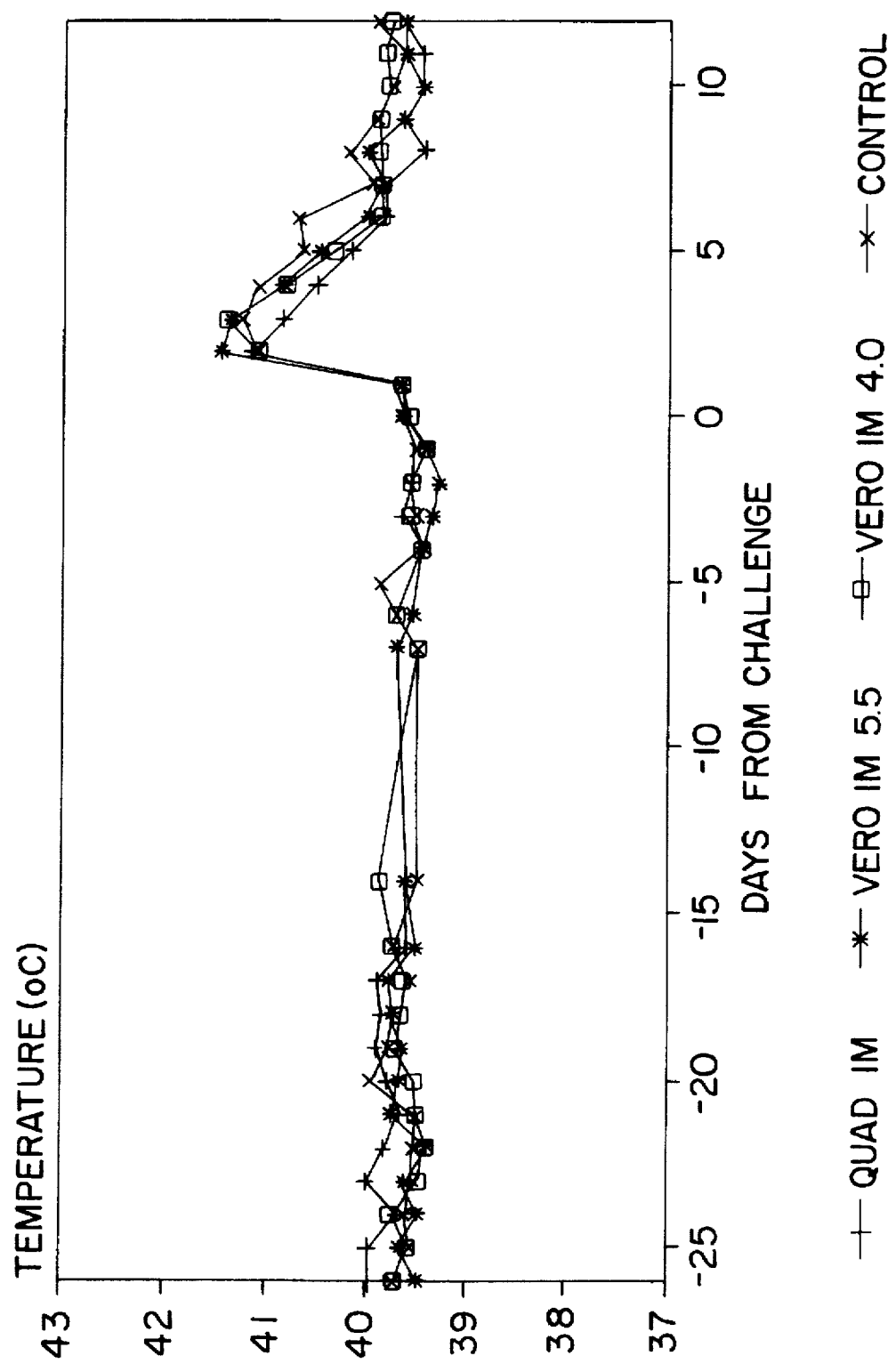
Figure 3:
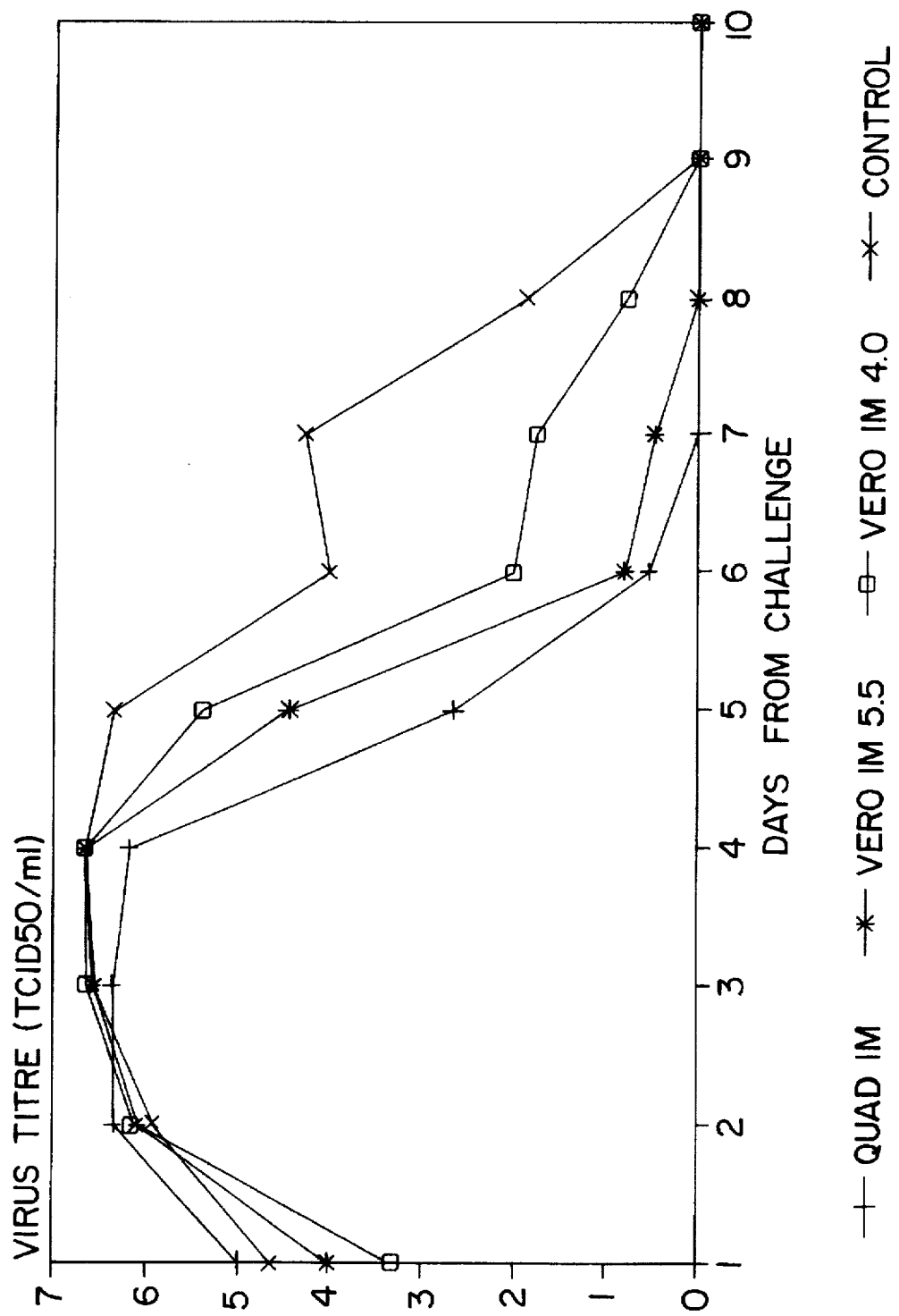
Figure 4:
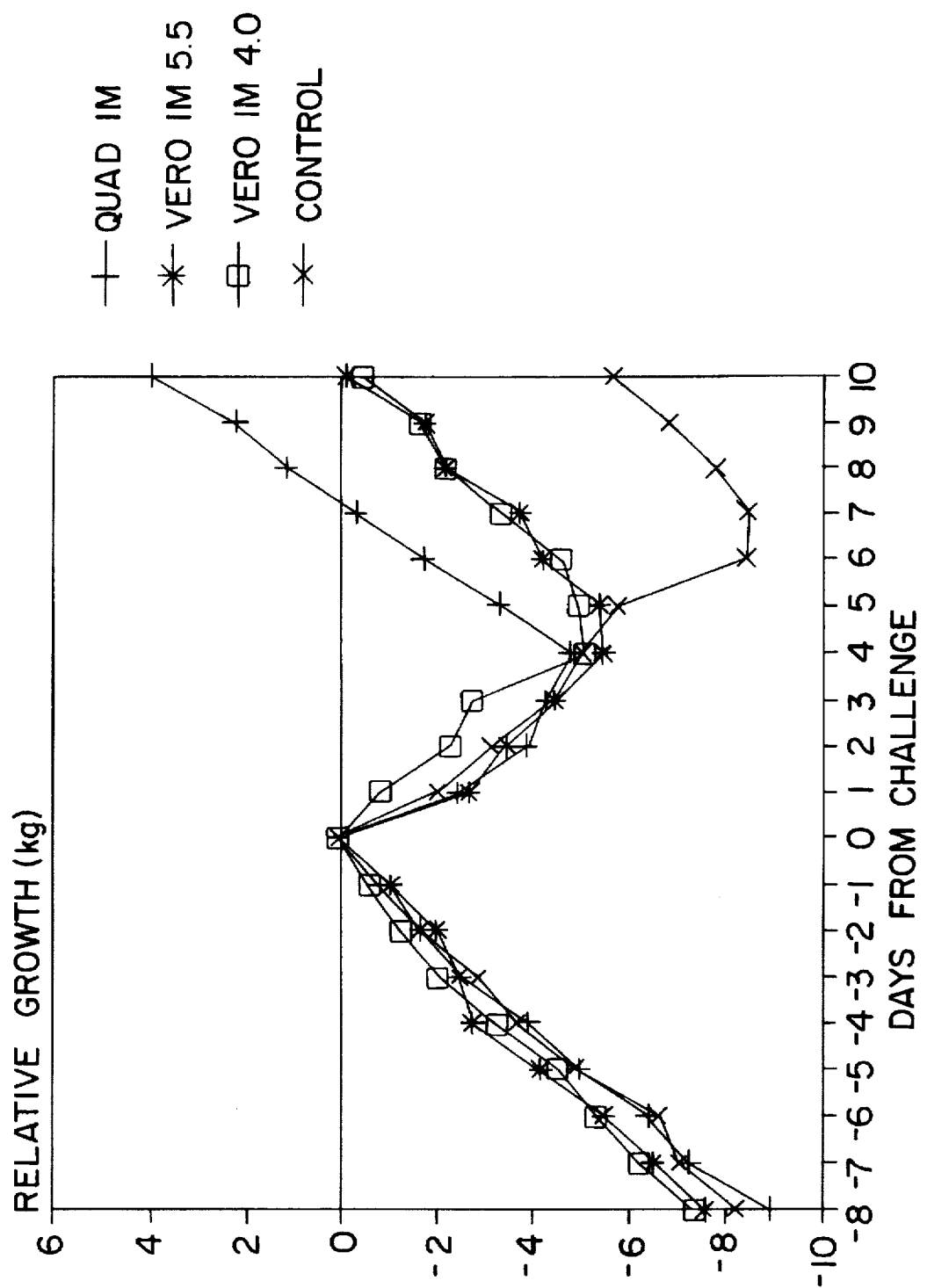

US005626850A

United States Patent [19]
Visser et al.

[11] Patent Number: 5,626,850
[45] Date of Patent: May 6, 1997

[54] NON-SHEDDING LIVE HERPESVIRUS VACCINE

[75] Inventors: Nicolaas Visser; Petrus A. M. van Woensel, both of Boxmeer, Netherlands; Thomas C. Mettenleiter, Tubingen, Germany

[73] Assignee: Akzo Nobel N.V., Arnhem, Netherlands

[21] Appl. No.: 211,278

[22] PCT Filed: Jun. 28, 1993

[86] PCT No.: PCT/EP93/01661

§ 371 Date: Mar. 28, 1994

§ 102(e) Date: Mar. 28, 1994

[87] PCT Pub. No.: WO94/03595

PCT Pub. Date: Feb. 17, 1994

[30] Foreign Application Priority Data

Jul. 30, 1992 [EP] European Pat. Off. ............. 92202370

[51] Int. Cl.$^6$ ............. A61K 39/245; A61K 39/295; C12N 7/00; C12N 5/10

[52] U.S. Cl. ............. 424/199.1; 424/205.1; 424/229.1; 424/93.21; 435/235.1

[58] Field of Search ............. 424/229.1, 199.1, 424/205.1, 184.1, 93.21, 93.3; 435/240.2, 235.1; 535/45

[56] References Cited

U.S. PATENT DOCUMENTS 5,240,703 8/1993 Cochran ............. 435/235.1

FOREIGN PATENT DOCUMENTS 9205263 4/1992 WIPO ............. C12N 15/86

OTHER PUBLICATIONS

Samulski, R.J. et al. 1989. Journal of Virology, vol. 63, pp. 3822–3828.

Morgenstern, J.P. et al. 1990. Nucleic Acids Research, vol. 18, pp. 3587–3596.

C. Marchioli et al., "Evaluation of pseudirabies virus glycoprotein gp50 as a vaccine for Aujesky's disease in mice and swine," J. Virol., vol. 61, No. 12, pp. 3977–3982, 1987.

D. Johnson et al., "Herpes Simplex viruses lacking glycoprotein D are unable inhibit virus penetration," J. Virol. vol. 62, No. 12, pp. 4605–4612, 1988.

B. Peeters et al., "Envelope glycoprotein gp50 of pseudorabies virus is essential for virus entry," J. Virol., vol. 67, No. 1, pp. 170–177, 1993.

I. Rauh et al., "Pseudorabies glcoproteins gII and gp50 are essential for virus penetration," J. Virol., vol. 65, No. 10, pp. 5348–5356, 1991.

B. Peeters et al., "Pseudorabies virus envelope glycoproteins are essential for virus penetration," J. Virol., vol. 66, No. 2, pp. 894–905, 1992.

N. De Wind et al., "Linker insertion mutagenesis of herpesvirus," J. Virol. vol. 64, No. 1o, pp. 4691–4696, 1990.

S. Heffner et al., "Glycoprotein gp50 negative pseudorabies virus," J. Virol., vol. 67, No. 3, pp. 1529–1537, 1993.

De, B.K. et al. 1988. Vaccine vol. 6 pp. 257–261.

Primary Examiner—Mary E. Mosher
Attorney, Agent, or Firm—Mary E. Gormley

[57] ABSTRACT

The present invention is concerned with a genetically modified live herpesvirus vaccine of which the live herpesviruses are not shed into the environment by a vaccinated animal. This can he achieved by deleting a gene encoding a gD homolog, such as gp50 of pseudorabies virus, and propagating this deletion mutant in a cell line expressing the gene product. The reduced shedding characteristic of such a vaccine is particularly advantageous in a vector vaccine. The present invention also concerns a quadruple mutant pseudorabies virus vaccine, and a live cell bound vaccine containing gp50 mutant pseudorabies virus and cells which do not complement the mutation.

**17

5,626,850

NON-SHEDDING LIVE HERPESVIRUS VACCINE

FIELD OF THE INVENTION

The present invention is concerned with a live herpesvirus vaccine.

BACKGROUND OF THE INVENTION P

Currently, several types of herpesvirus vaccines are being applied, i.e. inactivated virus vaccines, subunit vaccines and modified live virus (MLV) vaccines.

Inactivated virus vaccines have the advantage that they do not comprise live infective viral material obviating the possibility of reversion of the viruses to a virulent state.

However, inactivated virus vaccines and subunit vaccines require the production of large quantities of the active vaccine component and are expensive to produce. Furthermore, these types of vaccines also require several inoculations with the vaccine in the presence of an adjuvant in order to provide immunity which is effective and long lasting.

MLV vaccines have important advantages in that they induce a rapid and long lasting immune response, both humoral and cellular, without the need of large quantities of the active component in the absence of adjuvants.

However, these vaccines still bear the risk of the vaccine virus being shed into the environment by the vaccinated animal, in particular when the live vaccine is administered via the natural route, e.g. intranasally.

Although MLV vaccines have been proven to be safe and efficacious there is a risk that the vaccine viruses revert to a more virulent state, or that the MLV spreads to other animals which are more susceptible for the MVL vaccine virus.

In particular, for the purpose of risk assessment by regulatory authorities with respect to vaccines based on genetically modified organisms, especially live organisms expressing foreign genes, the aspect of possible shedding of these organisms in the environment is very important.

Thus, it can be appreciated that herpesvirus vaccines which display the advantages of live virus inoculation but which are confined to the vaccinated animals are highly desirable.

The envelope glycoproteins of herpesviruses are major targets of the immune response to herpes vital infection. Furthermore, these glycoproteins are important for the interaction of the virus with its host cell.

The pseudorabies virus (PRV) is a herpesvirus that causes an economically significant disease in swine called Aujeszky's disease. It has been well documented that the glycoprotein D (gD) homolog of PRV (glycoprotein 50, gp50) is a major immunogen of PRV which is the most potent for the induction of protective immunity in an infected host animal (Eloit, M. et al., Archs. Virol. 99, 45–56, 1988; Marchioli, C. et al., Am. J. Vet.res. 49, 860–864, 1988; Ishii, H. et al., J. Gen. Virol. 69, 1411–1414, 1988; Marchioli, C. C. et al., J. Virol. 61, 3977–3982, 1987; Wathen, M. W. et al., J. Virol. 51, 57–62, 1984, Mettenleiter, T. C., Comp. Immun. Microbiol. Infect. Dis. 14, 151–163, 1991).

Furthermore, Rauh, I. and Mettenleiter, T. C. (J. Virol. 65, 5348–5356, 1991), and Peeters, B. et al., (J. Virol. 66, 894–905, 1992) constructed a gp50-negative (gp50-) PRV mutant which is phenotypically gp50-positive as result of their growth in a cell line expressing gp50. It was concluded therein that for the in vitro replication of the virus gp50 is essential for penetration into a cell and is not required for cell-cell spread of the virus.

SUMMARY OF THE INVENTION

It is an object of the present invention to provide a live herpesvirus vaccine which is both effective in that it induces a protective immune response and safe because of a reduced level of shedding live viruses in the environment, thereby combining the potency of a MLV vaccine and the safety of an inactivated vaccine.

The invention is characterized in that the live herpesvirus vaccine comprise live herpesviruses which are not able to produce a functional gD homolog said herpesviruses being complemented with the gD homolog.

With gD homolog herein is meant the glycoprotein of the specific herpesvirus which exhibits significant homology to the well characterized glycoprotein D of the herpes simplex virus (HSV). Several herpesvirus gD homologs and the genes encoding these homologs have already been described in the prior art, such as the gD homolog of PRV, i.e.,gp50 (Petrovskis, E. A. et al., J. Virol. 59, 216–223, 1986), bovine herpesvirus-1, i.e. gIV (Tikoo, S. K. et al., J. Virol. 64, 5132–5142, 1990) and equine herpesvirus-1 (Flowers, C. C. et al., Virology 180, 175–184, 1991).

BRIEF DESCRIPTION OF THE DRAWINGS

FIG. 1. Genomic map of U.S. region of the PRV parent strain, the quadruple mutant, and the PRV gene fragment stably transformed into the MDBK cell line.

FIG. 2. Temperatures of the pigs vaccinated with the quadruple. mutant and unvaccinated pigs from 26 days before to 11 days after challenge. Vaccination was performed at day −12 and challenge at day 0.

FIG. 3. Virus excretion of the pigs vaccinated with the quadruple mutant and unvaccinated pigs from 1 day after challenge to 10 days after challenge.

FIG. 4. Relative growth of the pigs vaccinated with the quadruple mutant and unvaccinated pigs from 8 days before to 10 days after challenge.

DETAILED DESCRIPTION OF THE INVENTION

According to the present invention the live vaccine comprising live herpesviruses which according to a first feature are not able to produce a functional gD homolog in an infected animal, surprisingly induces a protective immune response in an inoculated host animal and is not shedded from the vaccinated animal.

A virus not able to produce a functional gD homolog is described as follows: upon replication of the virus in the host animal, the gD gene does not express a functional gene product.

A functional gD gene product is a gD gene product that makes it possible for purified herpesviruses to infect a suitable host cell.

This can be achieved by introducing a mutation into the gene encoding the gD homolog or into a region controlling the expression of said glycoprotein, preferably by utilizing recombinant DNA techniques.

A mutation is understood to be a change of the genetic information in the above-mentioned region with respect to the genetic information present in this region of the genome of naturally occurring herpes-viruses. The mutation is, for example, a nucleic acid substitution, deletion, insertion or inversion, or a combination thereof resulting in a herpesvirus which fails to produce a functional gD homolog. Preferably the mutation is a deletion and/or insertion.

Deletions may be produced for example by cleaving the gD homolog gene inserted into a vector by means of one or more appropriate restriction of the gD homolog gene, and thereafter ligating the vector DNA.

Alternatively, said gene may be cleaved at one site followed by exonuclease treatment in order to remove terminal nucleotides resulting in the complete or partial removal of the gene, and the ligating vector DNA. The result of this process is the modification of herpesvirus DNA such that no functional gD homolog gene product can be expressed any more due to for example alteration of the reading frame or removal of DNA sequences necessary for the coding of a functional gene product.

In a preferred embodiment of the invention a live herpesvirus vaccine is used comprising viruses containing a deletion in the genome comprising the whole gD homolog gene.

Insertions of heterologous DNA in the gD homolog gene of a herpesvirus may also result in the inability of the virus to express a functional gD homolog.

Insertions of heterologous DNA may be achieved by well known procedures such as those making use of double-stranded linkers containing one or more restriction enzyme sites, or by means of the homopolymer tailing technique. The term "heterologous DNA" means a DNA sequence which either does not encode a polypeptide or encodes a polypeptide other than the gD homolog gene of the same origin as the gene to be inactivated.

The length and sequence of the non-coding heterologous DNA are not critical and includes oligonucleotides, preferably of 8–50 nucleotides in length. A suitable double-stranded oligonucleotide comprises three translational stop codons in each of the possible reading frames in beth directions, in addition to appropriate restriction enzyme cleavage sites.

Well-known techniques can be used to produce the deletions and/or insertions in the gD homolog gene required in the present invention, such as for example the in vivo homologous recombination technique (Manjarls, T. et al., in "Molecular Cloning", second edition, Cold Spring Harber Laboratory, 1989; Roizman, B. and Jenkins, F. J., Science 229, 1208, 1985; Higuchi, R. et al., Nucleic Acids Res. 16, 7351, 1988).

Briefly, a DNA fragment comprising the gD homolog gene is isolated from the herpesvirus genomic DNA.

This fragment can then be cloned into a vector. Any bacterial plasmid or bacteriophage vector containing a selectable marker can be used therefore. Examples of such cloning vectors are plasmid pBR322 or derivatives thereof, the various pUC and Bluescript plasmids and bacteriophages lambda and M13.

Utilizing the recombinant vectors comprising the whole or a fragment of the gD homolog gene deletions and/or insertions of heterologous DNA therein can be effected as described above.

The recombinant vectors having the desired mutation can then be selected and propagated into a host cell using standard transformation procedures. Any host cell in which the vector can be propagated can be utilized. For example *E. coli* is a suitable host for the propagation of pBR322.

Thereafter, appropriate cells in which the respective gD homolog-negative herpesvirus is able to replicate are applied in standard co-transfection procedures whereby recombination occurs between corresponding regions in the recombinant vector and the herpesvirus genome.

Recombinant viral progeny is thereafter produced in cell culture and can be selected genotypically or phenotypically, e.g. by hybridization or by detecting enzyme activity or antigenic activity encoded by a gene introduced together with the mutation in the gD homolog gene. The desired herpesvirus can then be cultured on a large scale in an appropriate cell culture whereafter the viruses can be harvested from the cell culture.

Another way to obtain live herpesviruses which are not able to produce a functional gD homolog in an infected animal is by bringing the gD homolog gene under control of specific nucleotide sequences capable of regulating the expression of the gD homolog in such a way that the gD homolog is expressed in in vitro cell culture but is not expressed in the inoculated host animal. Examples of such expression control sequences are promoters and enhancers.

Preferably the gD homolog gene is placed under control of an inducible regulating nucleotide sequence. An inducible regulating nucleotide sequence of this type is, for example, a regulating nucleotide sequence which only comes into action under the influence of specific physical or chemical stimulation, such as hormones, pharmaceuticals, metal ions and the like. Suitable examples of such inducible regulating nucleotide sequences are the metallothione in promoter and heat shock promoter.

A preferred second feature of the live herpesviruses present in the vaccine according to the invention is that said herpesviruses are complemented with the gD homolog protein. Such viruses can be obtained by propagating the genotypically gD⁻ herpesviruses in an appropriate cell line, i.e. in a complementing cell line which is able to express the required gD homolog.

Such complementing cell lines can be obtained by transforming a cell line which is susceptible for the respective parental herpesvirus with a plasmid comprising the gD homolog gene using standard techniques such as transfection or electroporation.

Another way of providing a cell with the gD homolog is to infect the cell with a recombinant retrovirus carrying the gD homolog gene, or a non-integrating recombinant virus e.g. vaccinia virus carrying the gD homolog gene.

gD homolog producing cell lines can a.o. also be obtained by synchronous infection (i.e. coinfection) with the virus carrying the gD homolog gene and the herpesvirus being defective in gD synthesis.

Subsequently, cells can be tested for gD homolog expression by means of immunological screening.

Preferably, the vaccine virus according to the invention is produced on a complementing cell line which does not comprise herpesvirus DNA sequences which are homologous to DNA sequences in the mutant herpesvirus genome in order to prevent that the genotypically gD⁻ herpesviruses are rescued by the complementing cell line comprising the gD homolog gene.

The growth of a deficient virus on cells complementing a gene product for which the virus is deficient has the potential risk of "rescuing". Rescuing means regaining lost genetic information, in this case through the exchange of genetic information between the cell and the virus, specifically through the exchange between the correct cellular genetic information and the deficient viral genome. This then leads to the formation of viruses that, by having rescued their lost genetic information, regained their "parent-" character. This process is also called "reversion", and viruses that have e.g. by rescuing, regained lost information are therefore also called "revertants". In this specific case the rescued viruses would be both phenotypically and genotypically gD-homolog-positive and therefore fully infectious. This is of course a highly unlikely situation.

The main cause of rescuing is the exchange of genetic information by so-called homologous recombination. This phenomenon occurs, although with low frequency, when homologous DNA regions (i.e. regions with an identical or closely related DNA sequence) present at different locations (e.g. in cellular and viral DNA) exchange with each other. This process is a.o. described in "Biochemistry" (Sterner $3^d$ edition 1988, p. 688–693). It is obvious that when the left and right flanking sequences of the parent gD-homolog in the cell and the flanking sequences of the deficient gD-homolog in the vital genome both are present in the same cell, this could in principle lead to homologous recombination, and therefore the formation of wild-type virus. Such processes have been described by Cai et al (J. of Virol.; 62/8: 2596–2604 (1988)). Another example of homologous recombination is described by van Zijl et al (J. of Virol.; 62/6:2191–2195 (1988)) who use homologous recombination for the reconstitution of herpesviruses from fragments with overlapping homology.

The danger of homologous recombination can be avoided if the complementing cell does not contain sequences that are homologous to the viral DNA. This could e.g. be accomplished by deleting the genetic information for the gD-homolog from the virus including one or more nucleotides from flanking sequences, while providing the complementing cell with the genetic information for only the gD-homolog without flanking sequences.

Very rarely, and with an extremely low frequency, recombination occurs between non-homologous sequences. This has e.g. been described by Meyer et al (Nature; 341: 419 (1989)). This heterologous recombination can never be completely avoided since it is inherent to DNA-replication. If however only the left or right flanking sequence of the gD-homolog gene is removed, the other site remains prone to homologous recombination. If homologous recombination at that site happens together with a random heterologous recombination at the other site of the gD-homolog gene, this still leads to an unwanted rescue-event.

Therefore, in a preferred form of the vaccine according to the invention, the DNA-fragment that provides the gD-homolog complement contains no sequences that are homologous with viral DNA sequences at both the left and the right flanking region.

Alternatively, live herpesviruses which are genotypically $gD^-$ can be used for the preparation of a vaccine according to the invention without the need of propagation on a complementing cell line if the vaccine comprises said herpesviruses in a cell associated form, e.g. as a suspension of infected cells. It is possible to maintain a replicating cell line containing a replicative form of the virus, in the absence of gD homolog. Mixing cells of this cell line with virus-free cells of the same or a compatible cell line leads by cell-cell contact to infection of all the cells in the culture, thus prodding a means of concomitantly propagating viruses and virus-containing cells that are both phenotypically and genotypically free of gD homolog.

The cell line may comprise a herpes virus that is not able to produce a functional gD homolog as a result of a deletion and/or insertion in the gene encoding the gD homolog. It is obvious that the cell line may also comprise herpes viruses that have been provided with additional deletions such as e.g. $tk^-$ or $gI^-$ and/or heterologous genes as discussed above or below.

A live herpesvirus vaccine according to the present invention can be derived from the group consisting of pseudorabies virus, bovine herpesvirus, feline herpesvirus, Marek's disease virus and equine herpesvirus.

In a preferred embodiment of the invention a live herpesvirus vaccine is provided wherein the herpesviruses are pseudorabies viruses.

The gene encoding the gD homolog of PRV (gp50) has been localized and sequenced by Petrovskis et al. (supra). A gp50 complementing cell line can be derived from any susceptible cell line for example MDBK or BHK cells as described by Rauh and Mettenleiter (supra).

The gD homolog gene of BHV-1 (gpIV is disclosed by Tikoo, S. K. et al. (supra). BHV gpIV complementing cell lines can be derived from for example MDBK cells (Fehler, F. et al., supra).

The gD homolog gene of EHV-1 has been characterized by Flowers, C. C. et al. (ibid). EHV-1 susceptible cells from which a complementing cell line can be derived are for example BHK or Vero cells.

Other suitable cell lines to be used for the preparation of a vaccine according to the present invention are for example CRFK cells (FHV) or QT35 cells (MDV).

The herpesvirus mutants of the live herpesvirus vaccine according to the present invention preferably contain additional mutations which attenuate the herpesvirus or result in the introduction of a serologically identifiable marker. This can be achieved by introducing deletions or insertions by means of recombinant DNA techniques in virulence associated genes or genes encoding non-essential glycoproteins of the herpesviruses, respectively. The attenuation of several herpesviruses by means of deleting the whole or a part of the thymidine-kinase (tk) gene is well known in the art (PRV: U.S. Pat. No. 4,609,548: BHV-i: European patent application 0226029; FHV: PCT-application 90/01547; EHV-4: PCT-application 92/01045). Attenuation of herpesvirus virulence can also be achieved by introducing a deletion in the gene encoding protein-kinase (PCT-application 90/00119).

In addition, a serologically identifiable marker deletion comprising the gene for herpesvirus glycoproteins have also been described (PRV: gI, European patent application 0141458; gX, European patent applications 0263207; BHV-1: gIII, European patent application 0316658).

A preferred vaccine according to the present invention comprises live PRV being genotypically $gI^-$ and/or $tk^-$ in addition to $gp50^-$.

The present invention also provides a live herpesvirus vaccine which is able to induce protective immunity in an animal against said herpesvirus and featuring the reduced shedding characteristics as described above, and which in addition is capable of expressing a desired protein, preferably an antigen of a pathogen which is able to evoke a protective immune response against said pathogen.

In such vector vaccines a heterologous DNA sequence encoding a polypeptide not normally associated in nature with the respective herpesvirus is inserted into an insertion-region, i.e. a region which can be used for the incorporation of said heterologous DNA sequence without disrupting essential functions of the herpesvirus such as those necessary for infection or replication, including the gD homolog gene.

The specific heterologous DNA sequence encoding an antigen of a pathogen to be inserted into the genome of the herpesvirus is not critical and depends on the specificity of the herpesvirus mutants described above for the host animal. For example, the heterologous DNA sequence to be inserted into a live PRV vaccine according to the invention may encode antigens of porcine pathogens such as hog cholera virus, parvovirus, influenza virus, *Pasteurella multocida, Actinobacillus pleuropneumoniae, Streptococcus suis* or *Escherichia coli.*

An essential requirement for the expression of the heterologous DNA sequence by the herpesvirus mutant described above is an adequate promoter operably linked to the heterologous DNA sequence. It is obvious to those skilled in the art that the choice of a promoter extends to any eukaryotic, prokaryotic or viral promoter capable of directing gene transcription in cells infected by the herpesvirus mutant, such as the SV-40 promoter (Science 222, 524–527, 1983) or, e.g., the metallothione in promoter (Nature 296, 39–42, 1982) .or a heat shock promoter (Voellmy et al., Proc. Natl. Acad. Sci. USA 82, 4949–53, 1985) or the human cytomegalovirus IE promotor or other promotors present in the herpesvirus genome.

The preparation of vector virus vaccines derived from herpesviruses is well known in the art, as described in Ackermann, M., J. Vet. Med. B. 35, 379–396 (1988); Cole, G. C. et al., J. Virol. 64, 4930–4938, 1990 and European patent application no. 389, 034.

In addition to an immunogenically effective amount of the live herpesvirus mutants described above, a vaccine according to the present invention may also contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of Bayol F® or Marcol 52®, saponins or vitamin-E solubilisate.

The useful dosage to be administered will vary depending on the age, weight and mammal vaccinated, the mode of administration and the type of pathogen against which vaccination is sought.

A suitable dosage may for example range between about $10^4$–$10^7$ pfu/animal.

For administration to animals, the vaccine according to the presentation can be given inter alia intranasally, intradermally, subcutaneously or intramuscularly.

EXAMPLE 1

A) Construction of Genotypical gp50⁻, Phenotypical gp50⁺PRV Mutant

PRV strain NIA-3 was used as the parental strain in the experiments. Viruses were propagated on Madin-Darby bovine kidney (MDBK) cells.

For construction of a gp50- expressing cell line, a plasmid containing a PRV genomic BamHI-SalI DNA fragment (BamHI-7B) was cleaved with BstXI, which separates the gp50 gene from its putative 5'-terminal promoter elements. After blunt ending with T4 polymerase, BamHI linkers (BRL, Eggenstein, Germany) were inserted and the plasmid was religated. Cleavage with BamHI and SalI then released a 552-bp fragment containing the 5' part of the gp50 gene, which was cloned into pBR322. The complete gp50 gene was assembled by inserting a 3, 346-bp SalI-SphI fragment into the SalI site. Subsequent cleavage with BamHI and DraI excised a 2, 433-bp fragment that contains the complete expression unit encompassing the genes encoding gp50 and gp63 (gp50–63) and the 3'-terminal mRNA processing signals. This fragment was then cloned behind the mouse metallothione in promoter (Brinster, R. L. et al., Cel 27, 223–231, 1981) giving rise to plasmid pMT50–63. To establish stably transformed gp50-expressing cell lines, MDBK cells were cotransfected with plasmids pMT50–63 and pSV2-neo by the calcium phosphate precipitation method (Graham, F. L., et al., Virology 52, 456–467, 1973; Southern, P. J. et al., J. Mol.Appl. Genet. 1, 327–341, 1982).

Selection for G418-resistant colonies was performed as described in Rauh, I., et al., J. Virol. 65, 621–631, 1991. gp50 expression was verified by immunofluorescence analyses after induction of the promoter with 100 μm $ZnSO_4$. Cell line MT50-3 was selected for further studies.

For isolation of a gp50-negative PRV mutant a 3.5-kb SalI-BamHI expression cassette containing the *Escherichia coli* β-galactosidase gene under control of the PRV glycoprotein gX promoter (Mettenleiter, T. C. et al., J. Virol. Methods 30, 55–66, 1990) was inserted into the SalI site in the middle of the gp50 gene to produce plasmid TT133/III. Transient expression assays showed the capability of this clone to express functional β-galactosidase.

Plasmid TT133/III was cotransfected with PRV wild-type NIA-3 DNA into MT50-3 cells. After a complete cytopathic effect had been induced, the supernatant was harvested and clarified and the virus progeny was plated onto MT50-3 cells in serial dilutions. When plaques became visible after 2 days, the cells were overlaid with agarose medium containing 300 μg of Bluo-Gal (BRL) per ml. Blue-staining plaques were picked and purified three times on MT50-3 cells until all plaques stained blue under a Bluo-Gal overlay. This mutant was used for further experiments.

B) Vaccination Experiments in Mice

For analysis of the virulence of the different mutants, 6-week-old female BALB/c mice were infected intranasally with 10 μl of virus suspension containing $10^4$ PFU of either $gX^-$ or phenotypically complemented $gp50^-$ PRV. This infectious dose had previously been established as leading to 100% mortality in $gX^-$ PRV-infected animals while it was low enough to avoid inclusion of significant amounts of rescued virus in the inoculum. Mice were observed at least every 8 h for symptoms of PRV infection. Moribund animals were sacrificed, and brain homogenates were analyzed for the presence of infectious virus by titration on gII-expressing MT-3 cells in which wild-type and $gX^-$ PRV, phenotypically complemented $gp50^-$ PRV, and all putative rescued virions should be able to form plaques. To this end, brains were removed, snap frozen in liquid nitrogen, homogenized in minimum essential medium supplemented with 100 μg of gentamicin (Boshringer, Mannheim, Germany) per ml. and plated onto MT-3 monolayers. After 1 h of adsorption, the monolayer was extensively washed with phosphate-buffered saline (PBS) and overlaid with methylcellulose medium supplemented by gentamicin. Two to 3 days post infection (p.i.) plaques were counted. Organs for histological examination were taken from moribund mice infected intranasally with $10^5$ PFU in a 50-μl volume to increase the number of infected cells for microscopical analysis.

Influence of non-functional gp50 on the virulence of PRV for mice.

In vitro, phenotypically complemented gp50⁻ PRV after primary infection is able to spread by direct cell-to-cell transmission. To analyze how this in vitro phenotype translates into in vivo characteristics, mice were infected intranasally with $10^4$ PFU of either gX⁻ PRV (which behaves like the normal wild type) or phenotypically complemented gp50⁻ mutants of both strains NIA-3 and Ka. It appeared that after phenotypic complementation, the gp50⁻ mutants were able to induce symptoms and to cause death in all animals, similar to the isogenic gX⁻ mutants. In addition, the onset of symptoms and the mean time to death between wild-type and gp50⁻ mutant virus infection were not significantly different. Non-complemented gp50⁻ virions, as expected, did not lead to any signs of disease, reflecting their inability to infect target cells. These results indicate that after primary infection, gp50 is not necessary for virulence of PRV after intranasal infection of mice.

Detection of free infectious virus after infection of mice with phenotypically complemented gp50⁻ PRV.

gp50 is required for penetration of virions into target cells in vitro. Therefore, virions released after primary infection of non-complementing cells by phenotypically complemented virus mutants are noninfectious. To analyze whether similar results could be observed in vivo, brain homogenates of moribund gX⁻ or gp50⁻ PRV-infected mice which were killed at the same time without exhibiting any signs of disease were used for reisolation of virus on gII-expressing MT-3 cells (Table 1). On these cells, all putative infectious virions, either gX⁻ or phenotypically complemented or rescued gp50⁻ PRV, should be able to form plaques. Whereas reisolation of virus form all gX⁻ PRV-infected animals proved to be successful, no free infectious virus was detected after infection by phenotypically complemented gp50⁻ PRV despite the fact that the animals were moribund, showing profound symptoms. Infectious virus was also not recovered from the gII⁻ PRV-infected animals.

C) Vaccination Experiments in Pigs

Six-week-old littermates (three animals per group) were infected intranasally with $10^6$ PFU of gX-βgal (gX⁻) or gp50-βgal (gp50'), PRV mutants derived from strain NIA-3. They were observed for signs of disease such as respiratory or neurological symptoms and fever. Nasal swabs were taken daily and titrated on MT-3 cells to detect shedding of any infectious virus. Survivors of this experiment (one gX⁻ PRV infected animal died) were bled 27 days p.i. and neutralizing antibody titers as well as the presence of anti-gp50 antibodies were determined. Complement-dependent and -independent neutralization titers were determined with a plaque reduction assay. The titers indicated show serum dilutions yielding 50% plaque reduction. Eight weeks p.i., the animals were challenge-infected intranasally with $3\times10^8$ PFU of wild-type strain NIA-3. Again, they were observed for signs of disease, body temperature was recorded, and nasal swabs were analyzed for virus shedding.

Determination of gp50⁻ PRV virulence for pigs. To establish the behaviour of the virus mutants in PRV's natural host, three pigs at 6 weeks of age, were intranasally infected with $10^6$ PFU of gX⁻ or gp50⁻ mutants derived from the highly virulent NIA-3 strain. They were observed for signs of AD, and shedding of virus was monitored by analyzing nasal swabs. As can be seen in Table 2 (experiment A), pigs infected with the gX⁻ mutant exhibited severe respiratory and neurological symptoms. One moribund animal was sacrificed. All animals showed prolonged fever and virus excretion in nasal swabs. In contrast, after infection with phenotypically complemented gp50⁻ PRV, only mild, mainly respiratory symptoms occurred. The only other sign of disease was a slight weakness in the hind legs. Duration of fever was much reduced, and no infectious virus could be recovered from nasal swabs.

It can be concluded that deletion of gp50 from strain NIA-3 decreases its virulence for pigs, although the virus was obviously still able to cause respiratory distress and fever. Sera taken from the surviving animals at day 27 p.i. showed the presence of neutralizing antibodies in the gX⁻ and gp50⁻ PRV-infected group (Table 2).

It is highly surprising, that whereas deletion of gp50 does hardly or not at all influence the virulence of PRV in mice (see Example 1B), the virulence in pigs, being the natural hosts, is highly decreased.

Determination of protection against virulent challenge after infection by gp50⁻ PRV. To analyze whether animals after prior infection by gX⁻ or phenotypically complemented gp50⁻ PRV were protected from challenge with a virulent virus, all pigs were intranasally challenged 8 weeks after the first infection with $3\times10^8$ PFU of the highly virulent NIA-3 strain. Results are shown in Table 2 (experiment B). The gX⁻ PRV survivors showed the least reaction upon challenge infection, with only limited fever and no shedding of challenge virus. The gp50⁻ PRV-infected pigs exhibited very mild symptoms of AD but only limited fever, although some virus shedding did occur. In summary, the results demonstrate that infection of pigs with a phenotypically complemented gp50⁻ PRV mutant led to induction of a significant protective immune response.

EXAMPLE 2: Construction of a Quadruple PRV Mutant

To completely eliminate the formation of revertants, a quadruple mutant was made. This mutant has a deletion in the U.S. region spanning the gX, gp50, gp63, and the gI genes from PRV. In this mutant no PRV sequences overlapping with the gp50 expressing cell line on either side of the gp50 gene were present. Therefore homologous recombination between the gp50 of the cell line and the mutated PRV has become impossible (Cai et al., J. Virol. 62, 2596-2604 [1988]; Peeters et al., J. Virol. 66, 894-905 [1992]; Peeters et al., J. Virol. 66, 3388-3892 [1992]. From a vaccine point the gI gene has to be deleted because this gene is used to differentiate between vaccine viruses and wild-type viruses in the eradication programs. Further all these deletions should make the quadruple mutant very low pathogenic and safe to use.

Plasmid TT-264 contains a modified pBR322 that carries the multiple cloning site of plasmid pUC18, an approx. 300bp SalI/BamhI-fragment encompassing the promoter for the glycoprotein gX-gene. Into the BamHI-site of the gX-gene the β-galactosidase (LacZ) gene from E. Coli has been fused, resulting in the inactivation of this BamHI-site (Mettenleiter and Rauh, J. Virol. Methods 30, 55–66, 1990). At the 3'-site of the LacZ a 1.4 kb SphI/BamHI-fragment, encompassing the 3'-end of the PRV gI-gene, the 11K-gene, and the 5'-end of the 28K gene, was inserted in the remaining BamHI-site. This was done by first ligating the sticky BamHI-end of the 1.4 kb fragment to the BamHI-site at the 3'-end of the LacZ gene. Then, after creating blunt ends of the remaining BamHI/SphI-end with Klenow/T4-polymerase, the vector was blunt-end ligated which restores the BamHI-site at this location. The correct orientation was verified by restriction digests. The resulting plasmid now contains from the 5'-site to the 3'-site, the PRV gX promoter, the β-galactosidase gene, the 3'-site of the PRV gI-gene, the PRV11K-gene and the 5'-end of the PRV 28K-gene. This plasmid was then cotransfected with the DNA from the Kaplan strain of PRV by the calcium phosphate precipitation method (Graham et al. 1973. Virology 52, 456–467) in gp50 producing MDBK cells. The virus progeny was then screened for the appearance of a blue plaque phenotype. Blue plaques were picked, purified and analyzed by Southern blotting. The presence of the correct deletion starting at the gX promoter and ending at the 5'-site of the gI-gene, deleting the PRV the gX, gp50, gp63 and the 5'-part of the gI genes, was confined (FIG. 1). The virus progeny cultured on the gp50 expressing cell line was further used for vaccination experiments.

EXAMPLE 3: Construction of a gp50 Expressing Cell Line

To complement the quadruple PRV mutant phenotypically for the gp50 protein a gp50 expressing cell line was made.

The construction of a gp50-expressing cell line was done as described by Rauh et al. 1991, J. Virology 65, 5348–5356. A plasmid containing a PRV genomic BamHI-SalI DNA fragment was cleaved with BstXI, which separates the gp50 gene from its putative 5'-terminal promoter elements (Petrovskis, 1986, J. Virol. 59:216–223). After blunt ending with T4 polymerase, BamHI linkers (BRL) were inserted and the plasmid was religated. Cleavage with BamHI and SalI then released a 522-bp fragment containing the 5"-part of the gp50 gene, which was cloned into pBR322. The complete gp50 gene was assembled by inserting a 3,346-bp SalI-SphI fragment into the SalI site. Subsequent cleavage with BamHI and DraI excised a 2,433-bp fragment that contains the complete expression unit encompassing the genes encoding gp50 and gp63 and the 3'-terminal mRNA processing signals. This fragment was then cloned behind the mouse metallothione in promoter (Brinster et al. 1981. Cell 27, 223–231). To establish stable transformed gp50 expressing cell lines, this plasmid was cotransfected with the pSV2-neo plasmid (Southern et al. 1982. J. Mol. Appl. Genet. 1, 327–341) by the calcium phosphate precipitation method (Graham et al. 1973. Virology 52, 456–467) into MDBK cells. Selection for G418 resistant colonies was performed and the selected cells were selected for their expression of gp50 with a gp50 specific MAb.

EXAMPLE 4: Vaccination of Pigs with the Quadruple PRV Mutant

In an experiment with the quadruple PRV mutant, a group of 7, 4–5 weeks old, pigs were vaccinated intramuscularly with $10^5$ TCID50/animal. Three weeks after vaccination the 7 vaccinated and 5 untreated pigs were challenged intranasally with $10^7$ TCID50 of PRV strain 75 V19. The animals were monitored daily for clinical signs, temperature, weight gain, and virus excretion. After vaccination with the quadruple mutant no clinical signs or fever were observed.

After challenge 2 of the 5 controls died, fever was observed for 7.7+/−0.5 days, growth retardation for more then 11 days and virus excretion for 7+/−1.4 days. For the pigs vaccinated with the quadruple PRV mutant all pigs survived, fever was observed for 4.7+/−1.2 days, growth retardation for 5.5+/−1 days and virus excretion for 5.2+/−0.5 days. A clear priming effect was seen in comparison to the controls, the presence of neutralizing antibodies in the vaccinated pigs was seen sooner and the titres were significant higher as in the controls. A graph of the mean temperatures, virus excretion in nasal swaps, and relative growth is given in FIGS. 2, 3, and 4 respectively.

These results indicate that pigs vaccinated with a $gX^-$, $gp50^-$, $gp63^-$, and $gI^-$ PRV mutant are partially protected against clinical signs of Aujeszky's disease.

EXAMPLE 5: Cell Bound Quadruple Mutant

To obtain cells expressing pheno- and genotypically gp50 negative PRV, 5 μg of quadruple DNA was transfected in to Vero cells with the $CaCl^2$ method. To maintain and to propagate the quadruple expressing Veto cells the cells were maintained until the showed 70% CPE. Cells were then trypsinized, mixed at a ratio of 1:5 with uninfected Vero cells, and seeded at a density of $0.2\times10^6$ cells/cm$^2$. For titration, cells were diluted in medium, mixed with uninfected cells and then plated out.

EXAMPLE 6: Vaccination with the Cell Bound Quadruple Mutant

In an experiment with the cell bound quadruple PRV mutant, two groups of 7, 4–5 weeks old, pigs were vaccinated intramuscularly with $10^{5.5}$ Pfu/animal and $10^4$ Pfu/animal. Three weeks after vaccination the vaccinated and 5 untreated pigs were challenged intranasally with $10^7$ TCID50 of PRV strain 75 V19. The animals were monitored daily for; clinical signs, temperature weight gain, and virus excretion.

After vaccination with the cell bound quadruple mutant no clinical signs or fever were observed in either group.

In this experiment the same controls were used as for testing the phenotypically gp50-positive quadruple mutant. After challenge 2 of the 5 controls died, fever was observed for 7.7+/−0.5 days, growth retardation for more then 11 days and virus excretion for 7+/−1.4 days. For the pigs vaccinated with the cell bound quadruple PRV mutant all pigs survived. In the pigs vaccinated with $10^{-5.5}$ Pfu, fever was observed for 6.1+/−1.1 days, growth retardation for 8+/−1.5 days and virus excretion for 5.4+/−0.7 days. At challenge none of the vaccinated pigs had neutralizing antibodies for PRV. In the pigs vaccinated with $10^4$ Pfu, fever was observed for 6.3+/−2.6 days, growth retardation for 9.2+/−1.2 days and virus excretion for 6.9+/−0.8 days. At challenge none of the vaccinated pigs had neutralizing antibodies for PRV. A graph of the mean temperatures, virus excretion in nasal swaps, neutralizing antibodies and relative growth is given in FIGS. 2, 3, and 4 respectively.

After vaccination with the cell bound quadruple mutant both groups of animals are partially protected. In comparison to the controls fever, virus excretion, and growth retardation was observed for a shorter period. The effects on growth retardation are best seen in FIG. 4. Not only was the period of growth retardation significantly shorter in comparison to the controls, but also absolute loss of weight was significantly less than in the untreated animals. In this experiment it is not only shown that the quadruple mutant has a protective effect on a challenge with a wild type PRV, but it is also shown for the first time that protection of pigs can be induced by vaccination with complete cells harbouring a cell bound virus.

TABLE 1

Virus isolation from gX⁻ or gp50⁻ PRV-infected mice.

| Group | Days p.i. | Severity of symptoms[a] | Virus reisolation[b] |
|---|---|---|---|
| Ka | | | |
| gX⁻ | 4 | ++ | $2.6 \times 10^4$ |
| gp50⁻ | 4 | ++ | 0 |
| NIA-3 | | | |
| gX⁻ | 3 | ++ | $1.0 \times 10^4$ |
| gp50⁻ | 3 | ++ | 0 |

[a] Symptoms of AD prior to sacrifice, ++, severe; −, none.
[b] Brain homogenates of animals that were sacrificed in a moribund state at the indicated time after infection were titrated on gII-expressing MT-3 cells. Values are mean titers for groups of four animals each.

TABLE 2

Signs of disease in infected and challenge-infected pigs

| | Neutralization titer[b] | | Virus shedding[c] | | Severity of symptoms[d] | | Fever | | Death |
|---|---|---|---|---|---|---|---|---|---|
| Group[a] | Without complement | With complement | Days p.i. | Peak titer | Respiratory | Central nervous system | Days p.i. | Peak (°C.) | (death/total) |
| Experiment A | | | | | | | | | |
| gX⁻ | 1:20 | 1:1,000 | 2–10 | $1.5 \times 10^4$ | ++ | ++ | 2–9 | 41.4 | 1/3 |
| gp50− | 1:5 | 1:500 | —[e] | — | + | (+) | 2–5 | 40.5 | 0/3 |
| Experiment B | | | | | | | | | |
| gX⁻ | ND | ND | — | — | (+) | − | 1–3 | 41.2 | 0/2 |
| gp50− | ND | ND | 1 and 3 | $1 \times 10^3$ | + | − | 1–3 | 40.9 | 0/3 |

[a] For experiment A, animals were infected intranasally with $10^6$ PFU of phenotypically complemented gp50− mutants of PRV strain NIA-3. For experiment B, animals of experiment A were challenge-infected intranasally with $3 \times 10^8$ PFU of wild-type strain NIA-3.
[b] Values are mean titers leading to 50% plaque reduction without or with addition of complement.
[c] Nasal swabs were taken daily and analyzed for presence of infectious virus by titration on gII-expressing MT-3 cells. Duration of virus shedding and peak titers per nasal swab are indicated.
[d] Severity of symptoms is indicated: −, none: (+), weak: +, intermediate: ++, severe.
[e] —, absence of neutralizing antibodies, virus shedding, symptoms, or fever.
[f] ND, not done.

We claim:

1. A live pseudorabies virus vaccine, comprising: live pseudorabies viruses that are not able to produce a functional gp50 protein in an infected animal as the result of a mutation comprising the deletion of the entire gp50 gene; and a pharmaceutically acceptable carrier or diluent.

2. A live pseudorabies virus vaccine according to claim 1, wherein the pseudorabies viruses contain the gp50 protein.

3. A live pseudorabies virus vaccine according to claim 1, wherein the pseudorabies viruses are gX⁻ and/or tk⁻.

4. A live pseudorabies virus vaccine according to claim 1, wherein the genome of the pseudorabies viruses comprises a heterologous DNA sequence encoding an antigen of a pathogen.

5. A live pseudorabies virus vaccine according to claim 1, wherein the pseudorabies viruses are gX⁻.

6. A live pseudorabies virus vaccine according to claim 1, further comprising an adjuvant.

7. A method of vaccinating an animal against a pseudorabies virus, comprising administering to said animal an effective amount of the vaccine according to claim 1.

8. A live pseudorabies virus vaccine, comprising: non-complementing cells harboring, in a cell-associated form, live pseudorabies viruses that are not able to produce a functional gp50 in an infected animal as a result of a mutation in the gp50 gene or the region controlling the expression thereof; and a pharmaceutically acceptable carrier or diluent.

9. A live pseudorabies virus vaccine according to claim 8, wherein the pseudorabies viruses are not able to produce a functional gp50 protein as a result of a deletion and/or insertion in the gene encoding the gp50 protein.

10. A pseudorabies virus vaccine according to claim 8, wherein, in addition to the mutation in the gp50 gene or the region controlling the expression thereof, the pseudorabies viruses are gI⁻ and/or tk⁻.

11. A pseudorabies virus vaccine according to claim 8, wherein the genome of the pseudorabies viruses comprises a heterologous DNA sequence encoding an antigen of a pathogen.

12. A live pseudorabies virus vaccine according to claim 8, further comprising an adjuvant.

13. A process for producing a live pseudorabies virus vaccine, wherein said vaccine comprises live pseudorabies viruses that are not able to produce a functional gp50 protein in an infected animal as a result of a mutation in the gp50 gene or in a region controlling the expression thereof, and a pharmaceutically acceptable carrier or diluent, wherein said pseudorabies viruses contain the gp50 protein, comprising the steps of:

a) propagating pseudorabies viruses in a gp50 complementing cell culture, wherein the DNA fragment of the cells that provides the gp50 complement contains no sequences at both the right and the left terminal regions of the gp50 gene that are homologous with the viral DNA sequences;

b) harvesting the pseudorabies viruses from the culture; and c) mixing the harvested pseudorabies viruses with a pharmaceutically acceptable carrier or diluent.

14. A process according to claim 13, wherein the pseudorabies viruses are not able to produce a functional gp50 protein as a result of a deletion and/or insertion of the gene encoding the gp50 protein.

15. A process according to claim 13, wherein the pseudorabies viruses are gX⁻ and/or tk⁻.

16. A process according to claim 13, wherein the genome of the pseudorabies viruses comprises a heterologous DNA sequence encoding an antigen of a pathogen.

17. A process according to claim 13, wherein the vaccine further comprises an adjuvant.

* * * * *

UNITED STATES PATENT AND TRADEMARK OFFICE
CERTIFICATE OF CORRECTION

PATENT NO. : 5,626,850
DATED : May 6, 1997
INVENTOR(S) : Visser et al.

It is certified that error appears in the above-indentified patent and that said Letters Patent is hereby corrected as shown below:

Please correct claim 8, column 14, line 2, by deleting "qp50" and replacing with -- gp50 --.

Signed and Sealed this

Thirtieth Day of September, 1997

Attest:

BRUCE LEHMAN

Attesting Officer

Commissioner of Patents and Trademarks